United States Patent
Morschhauser et al.

(10) Patent No.: US 6,964,995 B2
(45) Date of Patent: Nov. 15, 2005

(54) GRAFTED COMB POLYMERS BASED ON ACRYLOYLDIMETHYLTAURINE ACID

(75) Inventors: Roman Morschhauser, Mainz (DE); Matthias Löffler, Niedernhausen (DE); Ilka Maier, Obertshausen (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/433,115

(22) PCT Filed: Nov. 28, 2001

(86) PCT No.: PCT/EP01/13855
§ 371 (c)(1),
(2), (4) Date: Nov. 17, 2003

(87) PCT Pub. No.: WO02/44268
PCT Pub. Date: Jun. 6, 2002

(65) Prior Publication Data
US 2004/0116628 A1 Jun. 17, 2004

(30) Foreign Application Priority Data
Dec. 1, 2000 (DE) .......................... 100 59 829

(51) Int. Cl.⁷ ................ C08L 51/00; C08F 2/22; C08F 271/02; C08F 291/00
(52) U.S. Cl. .............. 525/68; 525/291; 424/70.1; 514/772.4; 514/937
(58) Field of Search ............... 525/68, 291; 514/772.4, 514/937; 424/70.1

(56) References Cited

U.S. PATENT DOCUMENTS

| | | | |
|---|---|---|---|
| 3,765,885 A | * 10/1973 | Bedell | 430/216 |
| 4,521,578 A | 6/1985 | Chen et al. | |
| 4,859,458 A | 8/1989 | Salamone et al. | |
| 5,296,218 A | 3/1994 | Chen et al. | |
| 5,368,850 A | 11/1994 | Cauwet et al. | 424/70 |
| 5,688,514 A | 11/1997 | Chaudhry et al. | |
| 5,837,789 A | 11/1998 | Stockhausen et al. | |
| 5,879,718 A | 3/1999 | Sebillote-Arnaud | 424/705 |
| 6,001,379 A | 12/1999 | Griat | 424/401 |
| 6,120,780 A | 9/2000 | Dupuis et al. | 424/401 |
| 6,395,853 B1 | 5/2002 | Oswald et al. | |
| 6,645,476 B1 * | 11/2003 | Morschhauser et al. | 424/70.1 |

FOREIGN PATENT DOCUMENTS

| | | |
|---|---|---|
| CA | 2363079 | 8/2000 |
| EP | 0 356 241 | 2/1990 |
| EP | 0 603 019 | 6/1994 |
| EP | 0 642 781 | 3/1995 |
| EP | 0 815 828 | 1/1998 |
| EP | 0 815 844 | 1/1998 |
| EP | 0 816 403 | 1/1998 |
| WO | WO 98/00094 | 1/1998 |

* cited by examiner

Primary Examiner—James J. Seidleck
Assistant Examiner—Irina S. Zemel
(74) Attorney, Agent, or Firm—Richard P. Silverman

(57) ABSTRACT

The invention provides water-soluble or water-swellable copolymers obtained by free-radical copolymerization of A) acryloyldimethyltaurine and/or acryloyldimethyltaurates, B) optionally, one or more other olefinically unsaturated, noncationic, optionally crosslinking comonomers containing at least one oxygen, nitrogen, sulfur or phosphorus atom and possessing a molecular weight of less than 500 g/mol, C) one or more mono- or polyolefinically unsaturated, optically crosslinking macromonomers each possessing at least one oxygen, nitrogen, sulfur or phosphorus atom and having a number-average molecular weight of greater than or equal to 200 g/mol, and D) taking place in the presence of at least one polymeric additive having number-average molecular weight of from 200 g/mol to $10^9$ g/mol.

The water-soluble or water-swellable copolymers of the present invention are useful in formulating cosmetics.

20 Claims, No Drawings

GRAFTED COMB POLYMERS BASED ON ACRYLOYLDIMETHYLTAURINE ACID

The present invention relates to grafted comb polymers based on acryloyldimethyltaurine and/or acryloyldimethyltaurates.

In recent years water-soluble polymers have acquired a continually increasing importance in industry and science. In volume terms, polyelectrolytes are occupying a very large proportion of the overall annual production. They find application, for example, in paper processing, in the laundry detergents industry, in textile processing, in petroleum extraction or as important base materials for cosmetics.

In the cosmetics sector a key role is accorded to polyelectrolytes. Besides water-soluble surface-active substances there is a high demand in this sector for systems which thicken oil and water. Thickeners of this kind, particularly the "superabsorbents" prepared on the basis of polyacrylic acid, have progressed since their development in the 1970s to become a pillar of the hygiene sector. In their crosslinked versions, partly or fully neutralized polyacrylic acids and their water-soluble copolymers are employed in numerous cosmetic formulations as bodying agents. The diversity of possible structures and the diverse possible applications associated therewith are manifested not least in a host of patents filed worldwide since the mid-1970s.

In the 1990s, innovative thickeners based on acryloyldimethyltaurine (AMPS) and the salts thereof were introduced into the market (EP 816 403 and WO 98/00094). In both homopolymer and copolymer form (®Aristoflex AVC, Clariant GmbH) such thickeners are superior in many respects to the corresponding polycarboxylates (Carbopols). For example, thickener systems based on AMPS display outstanding properties in pH ranges below pH 6, i.e., in a pH range in which it is no longer possible to operate with conventional polycarboxylate thickeners. The ease of processing and the favorable toxicological profile of the principal monomer imbue these thickeners with a high application potential. Moreover, the microgel structure of such thickeners leads to a particularly pleasant skin sensation.

A disadvantage of thickeners based on acryloyldimethyltaurine is the frequently occurring opalescence of their dilute aqueous gels. The cause of the opalescence is the strong scattering of visible light by overcrosslinked polymer fractions which arise in the course of the polymerization and are present in only inadequately swollen form in water.

Surprisingly it has been found that grafted comb polymers based on acryloyldimethyltaurine (AMPS) and obtainable by conducting the polymerization in the presence of a polymeric additive possess very good thickening and emulsifying/dispersing properties and, moreover, exhibit a clear appearance.

The invention provides water-soluble or water-swellable copolymers obtainable by free-radical copolymerization of
A) acryloyldimethyltaurine and/or acryloyldimethyltaurates,
B) if desired, one or more other olefinically unsaturated, optionally crosslinking comonomers containing at least one oxygen, nitrogen, sulfur or phosphorus atom and possessing a molecular weight of less than 500 g/mol, and
C) one or more olefinically mono- or polyunsaturated, optically crosslinking macromonomers each possessing at least one oxygen, nitrogen, sulfur or phosphorus atom and having a number-average molecular weight of greater than or equal to 200 g/mol, the copolymerization
D) taking place in the presence of at least one polymeric additive having number-average molecular weights of from 200 g/mol to $10^9$ g/mol.

The copolymers of the invention preferably possess a molecular weight of from $10^3$ g/mol to $10^9$ g/mol, more preferably from $10^4$ to $10^7$ g/mol, very preferably from $5*10^4$ to $5*10^6$ g/mol.

The acryloyldimethyltaurates can be the organic or inorganic salts of acryloyldimethyltaurine. Preference is given to the $Li^+$, $Na^+$, $K^+$, $Mg^{++}$, $Ca^{++}$, $Al^{+++}$ and/or $NH_4^+$ salts. Likewise preferred are the monoalkylammonium, dialkylammonium, trialkylammonium and/or tetraalkylammonium salts, in which the alkyl substituents of the amines may independently of one another be $(C_1-C_{22})$-alkyl radicals or $(C_2-C_{10})$-hydroxyalkyl radicals. Preference is also given to mono- to triethoxylated ammonium compounds with a different degree of ethoxylation. It should be noted that the invention also embraces mixtures of two or more of the abovementioned representatives.

The degree of neutralization of the acryloyldimethyltaurine can be between 0 and 100%, particular preference being given to a degree of neutralization of more than 80%.

Based on the total mass of the copolymers, the amount of acryloyldimethyltaurine and/or acryloyldimethyltaurates is at least 0.1% by weight, preferably from 20 to 99.5% by weight, more preferably from 50 to 98% by weight.

As comonomers B) it is possible to use all olefinically unsaturated monomers whose reaction parameters allow copolymerization with acryloyldimethyltaurine and/or acryloyldimethyltaurates in the respective reaction media.

Preferred comonomers B) are unsaturated carboxylic acids and their anhydrides and salts, and also their esters with alliphatic, olefinic, cycloalliphatic, arylalliphatic or aromatic alcohols having a carbon number of from 1 to 22.

Particularly preferred unsaturated carboxylic acids are acrylic acid, methacrylic acid, styrenesulfonic acid, maleic acid, fumaric acid, crotonic acid, itaconic acid, and senecic acid.

Preferred counterions are $Li^+$, $Na^+$, $K^+$, $Mg^{++}$, $Ca^{++}$, $Al^{+++}$, $NH_4^+$, monoalkylammonium, dialkylammonium, trialkylammonium and/or tetraalkylammonium radicals, in which the alkyl substituents of the amines independently of one another can be $(C_1-C_{22})$-alkyl radicals or $(C_2-C_{10})$-hydroxyalkyl radicals. It is additionally possible to employ mono- to triethoxylated ammonium compounds with a different degree of ethoxylation. The degree of neutralization of the carboxylic acids can be between 0 and 100%.

Further preferred comonomers are open-chain N-vinyl amides, preferably N-vinylformamide (VIFA), N-vinylmethylformamide, N-vinylmethylacetamide (VIMA) and N-vinylacetamide; cyclic N-vinyl amides (N-vinyl lactams) with a ring size of 3 to 9, preferably N-vinylpyrrolidone (NVP) and N-vinylcaprolactam; amides of acrylic and methacrylic acid, preferably acrylamide, methacrylamide, N,N-dimethylacrylamide, N,N-diethylacrylamide, and N,N-diisopropylacrylamide; alkoxylated acrylamides and methacrylamides, preferably hydroxyethyl methacrylate, hydroxymethylmethacrylamide, hydroxyethylmethacrylamide, hydroxypropylmethacrylamide, and mono [2-(methacryloyloxy)ethyl] succinate; N,N-dimethylamino methacrylate; diethylaminomethyl methacrylate; acrylamido- and methacrylamidoglycolic acid; 2- and 4-vinylpyridine; vinyl acetate; glycidyl methacrylate; styrene; acrylonitrile; vinyl chloride; stearyl acrylate; lauryl methacrylate; vinylidene chloride; and/or tetrafluoroethylene.

Likewise suitable comonomers B) are inorganic acids and their salts and esters. Preferred acids are vinylphosphonic acid, vinylsulfonic acid, allylphosphonic acid, and methallylsulfonic acid.

The weight fraction of the comonomers B), based on the total mass of the copolymers, can be from 0 to 99.7% by weight and is preferably from 0.5 to 80% by weight, more preferably from 2 to 50% by weight.

In accordance with the invention the copolymerization is carried out using at least one macromonomer C), as it is called. The macromonomers are at least singly olefinically functionalized polymers having one or more discrete repeating units and a number-average molecular weight of greater than or equal to 200 g/mol. In the copolymerization it is also possible to use mixtures of chemically different macromonomers C). The macromonomers are polymeric structures composed of one or more repeating units and have a molecular weight distribution characteristic of polymers.

Preferred macromonomers C) are compounds of formula (I).

$R^1$ represents a polymerizable function from the group of the vinylically unsaturated compounds which are suitable for constructing polymeric structures by a free-radical route. Preferably $R^1$ is a vinyl, allyl, methallyl, methylvinyl, acryloyl ($CH_2=CH-CO-$), methacryloyl ($CH_2=C[CH_3]-CO-$), crotonyl, senecionyl, itaconyl, maleyl, fumaryl or styryl radical.

Attachment of the polymer chain to the reactive end group requires a suitable bridging group Y. Preferred bridges Y are $-O-$, $-C(O)-$, $-C(O)-O-$, $-S-$, $-O-CH_2-CH(O-)-CH_2OH$, $-O-CH_2-CH(OH)-CH_2O-$, $-O-SO_2-O-$, $-O-SO_2-O-$, $-O-SO-O-$, $-PH-$, $-P(CH_3)-$, $-PO_3-$, $-NH-$, and $-N(CH_3)-$, more preferably $-O-$.

The polymeric central moiety of the macromonomer is represented by the discrete repeating units A, B, C, and D. Preferred repeating units A, B, C, and D are derived from acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, and diisopropylacrylamide, especially from ethylene oxide and propylene oxide.

The indices v, w, x, and z in formula (I) represent the stoichiometric coefficients relating to the repeating units A, B, C, and D. v, w, x, and z amount independently of one another to from 0 to 500, preferably 1 to 30, it being necessary for the sum of the four coefficients on average to be $\geq 1$.

The distribution of the repeating units over the macromonomer chain can be random, blocklike, alternating or gradientlike.

$R^2$ denotes a linear or branched alliphatic, olefinic, cycloalliphatic, arylalliphatic or aromatic ($C_1-C_{50}$) hydrocarbon radical, OH, $-NH_2$, $-N(CH_3)_2$ or is the structural unit $[-Y-R^1]$.

In the case of $R^2$ being $[-Y-R^1]$ the macromonomers in question are difunctional and suitable for crosslinking the copolymers.

Particularly preferred macromonomers C) are acrylically or methacrylically monofunctionalized alkyl ethoxylates of formula (II).

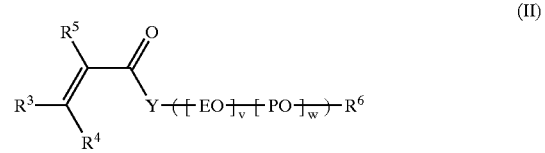

$R_3$, $R_4$, $R_5$, and $R_6$ are independently of one another hydrogen or n-alliphatic, iso-alliphatic, olefinic, cycloalliphatic, arylalliphatic or aromatic ($C_1-C_{30}$) hydrocarbon radicals.

Preferably $R_3$ and $R_4$ are H or $-CH_3$, more preferably H; $R_5$ is H or $-CH_3$; and $R_6$ is an n-alliphatic, iso-alliphatic, olefinic, cycloalliphatic, arylalliphatic or aromatic ($C_1-C_{30}$) hydrocarbon radical.

v and w are in turn the stoichiometric coefficients relating to the ethylene oxide units (EO) and propylene oxide units (PO). v and w amount independently of one another to from 0 to 500, preferably 1 to 30, it being necessary for the sum of v and w to be on average $\geq 1$. The distribution of the EO and PO units over the macromonomer chain can be random, blocklike, alternating or gradientlike. Y stands for the above-mentioned bridges.

Particularly preferred macromonomers C) have the following structure in accordance with formula (II):

| Name | $R^3$ | $R^4$ | $R^5$ | $R^6$ | v | w |
|---|---|---|---|---|---|---|
| ® LA-030 methacrylate | H | H | $-CH_3$ | -lauryl | 3 | 0 |
| ® LA-070 methacrylate | H | H | $-CH_3$ | -lauryl | 7 | 0 |
| ® LA-200 methacrylate | H | H | $-CH_3$ | -lauryl | 20 | 0 |
| ® LA-250 methacrylate | H | H | $-CH_3$ | -lauryl | 25 | 0 |
| ® T-080 methacrylate | H | H | $-CH_3$ | -talc | 8 | 0 |
| ® T-080 acrylate | H | H | H | -talc | 8 | 0 |
| ® T-250 methacrylate | H | H | $-CH_3$ | -talc | 25 | 0 |
| ® T-250 crotonate | $-CH_3$ | H | $-CH_3$ | -talc | 25 | 0 |
| ® OC-030 methacrylate | H | H | $-CH_3$ | -octyl | 3 | 0 |
| ® OC-105 methacrylate | H | H | $-CH_3$ | -octyl | 10 | 5 |
| ® Behenyl-010-methylaryl | H | H | H | -behenyl | 10 | 0 |
| ® Behenyl-020-methylaryl | H | H | H | -behenyl | 20 | 0 |
| ® Behenyl-010-senecionyl | $-CH_3$ | $-CH_3$ | H | -behenyl | 10 | 0 |
| ® PEG-440 diacrylate | H | H | H | -acryloyl | 10 | 0 |
| ® B-11-50 methacrylate | H | H | $-CH_3$ | -butyl | 17 | 13 |
| ® MPEG-750 methacrylate | H | H | $-CH_3$ | -methyl | 18 | 0 |
| ® P-010 acrylate | H | H | H | -phenyl | 10 | 0 |
| ® O-050 acrylate | H | H | H | -oleyl | 5 | 0 |

The molecular weight of the macromonomers C) is preferably from 200 g/mol to $10^6$ g/mol, more preferably from 150 to $10^4$ g/mol, and very preferably from 200 to 5000 g/mol.

Based on the total mass of the copolymers it is possible for the weight fraction of the macromonomer C) to be from 0.1 to 99.8% by weight, more preferably from 2 to 90% by weight, very preferably from 5 to 80% by weight.

Essential for the invention is that the copolymerization is conducted in the presence of at least one polymeric additive D), the additive D) being added wholly or partly in solution to the polymerization medium before the actual copolymerization. The use of two or more additives D) is likewise in accordance with the invention. Crosslinked additives D) may likewise be used.

The additives D) or mixtures thereof must only be wholly or partly soluble in the chosen polymerization medium.

During the actual polymerization step the additive D) has a number of functions. On the one hand it prevents the formation of overcrosslinked polymer fractions in the copolymer which forms in the actual polymerization step, and on the other hand the additive D) is statistically attacked by active free radicals in accordance with the very well-known mechanism of graft copolymerization. Depending on the particular additive D), this results in greater or lesser fractions of the additive being incorporated into the copolymers. Moreover, suitable additives D) possess the property of altering the solution parameters of the copolymers which form during the free-radical polymerization reaction in such a way that the average molecular weights are shifted to higher values. As compared with analogous copolymers prepared without the addition of the additives D), those prepared with the addition of additives D) advantageously exhibit a significantly higher viscosity in aqueous solution.

Preferred additives D) are homopolymers and copolymers which are soluble in water and/or alcohols. The term "copolymers" also comprehends those having more than two different monomer types.

Particularly preferred additives D) are homopolymers and copolymers of N-vinylformamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxyethyl methacrylate, diallyldimethylammonium chloride (DADMAC) and/or [2-(methacryloyloxy)ethyl] trimethylammonium chloride (MAPTAC); polyalkylene glycols and/or alkylpolyglycols.

Particularly preferred additives D) are polyvinylpyrrolidones (e.g., K15®, K20® and K30® from BASF), poly(N-vinylformamides), poly(N-vinylcaprolactams), and copolymers of N-vinylpyrrolidone, N-vinylformamide and/or acrylic acid, which may also have been partly or fully hydrolyzed.

The molecular weight of the additives D) is preferably from $10^2$ to $10^7$ g/mol, more preferably from $0.5*10^4$ to $10^6$ g/mol.

The amount of polymeric additives D), based on the total mass of the copolymers, is from 0.1 to 99.8% by weight, preferably from 0.1 to 90% by weight, more preferably from 1 to 20% by weight, with particular preference from 1.5 to 10% by weight.

In one further preferred embodiment the copolymers of the invention are crosslinked, i.e., they contain comonomers containing at least two polymerizable vinyl groups.

Preferred crosslinkers are methylenebisacrylamide; methylenebismethacrylamide; esters of unsaturated monocarboxylic and polycarboxylic acids with polyols, preferably di-acrylates and tri-acrylates and -methacrylates, more preferably butanediol and ethylene glycol diacrylate and -methacrylate, trimethylolpropane triacrylate (TMPTA) and allyl compounds, preferably allyl (meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives.

A particularly preferred crosslinker is trimethylolpropane triacrylate (TMPTA).

The weight fraction of crosslinking comonomers, based on the total mass of the copolymers, is preferably up to 20% by weight, more preferably from 0.05 to 10% by weight, and very preferably from 0.1 to 7% by weight.

The polymerization medium used may comprise all organic or inorganic solvents which have a very substantially inert behavior with respect to free-radical polymerization reactions and which advantageously allow the formation of medium or high molecular weights. Those used preferably include water; lower alcohols; preferably methanol, ethanol, propanols, iso-, sec- and t-butanol, very preferably t-butanol; hydrocarbons having 1 to 30 carbon atoms, and mixtures of the aforementioned compounds.

The polymerization reaction takes place preferably in the temperature range between 0 and 150° C., more preferably between 10 and 100° C., either at atmospheric pressure or under elevated or reduced pressure. If desired the polymerization may also be performed under an inert gas atmosphere, preferably under nitrogen.

In order to initiate the polymerization it is possible to use high-energy electro-magnetic rays, mechanical energy, or the customary chemical polymerization initiators, such as organic peroxides, e.g., benzoyl peroxide, tert-butyl hydroperoxide, methyl ethyl ketone peroxide, cumene hydroperoxide, dilauroyl peroxide (DLP) or azo initiators, such as azodiisobutyronitrile (AIBN), for example. Likewise suitable are inorganic peroxy compounds, such as $(NH_4)_2S_2O_8$, $K_2S_2O_8$ or $H_2O_2$, for example, where appropriate in combination with reducing agents (e.g., sodium hydrogensulfite, ascorbic acid, iron(II) sulfate, etc.) or redox systems comprising as reducing component an alliphatic or aromatic sulfonic acid (e.g., benzenesulfonic acid, toluenesulfonic acid, etc.).

The polymerization reaction can be conducted, for example, as a precipitation polymerization, emulsion polymerization, bulk polymerization, solution polymerization or gel polymerization. Particularly advantageous for the profile of properties of the copolymers of the invention is precipitation polymerization, preferably in tert-butanol.

The polyfunctional copolymers of the invention possess a high structural diversity and, consequently, broad potential application possibilities, which can be tailored to virtually any task where interface or surface effects play a part. The intention is also in particular to point out the possibilities for use in the field of cosmetology, as thickeners and emulsifiers, for example. The term "tailored-made polymers" illustratively describes the possibilities which this new class of polymer puts at the disposal of the user.

The following examples are intended to illustrate the invention without, however, restricting it thereto.

EXAMPLE 1

| Reactants | amount (g) |
| --- | --- |
| $NH_3$-neutralized AMPS | 80 |
| ® Genapol-LA-070 methacrylate | 20 |
| t-Butanol | 400 |
| TMPTA | 1.8 |
| Dilauroyl peroxide (initiator) | 1 |
| Poly-N-vinylpyrrolidone (® K-15, BASF) | 5 |

The polymer was prepared by the precipitation method in tert-butanol. The monomers in t-butanol were introduced as an initial charge and then the reaction mixture, after initial heating to 60° C., was initiated by addition of DLP. The polymer was isolated by removing the solvent under suction and by subsequent vacuum drying.

The polymer showed a clear appearance with a viscosity of 45 000 mPas in 1% strength solution in distilled water. In comparison thereto, the unmodified gel of the same composition—only the polymeric additive is absent—exhibits a much more opalescent appearance and a viscosity of 40 000 mPas under identical measurement conditions.

EXAMPLE 2

| Reactants | amount (g) |
|---|---|
| $NH_3$-neutralized AMPS | 70 |
| N-Vinylpyrrolidone | 5 |
| ® Genapol-T-250 methacrylate | 15 |
| Water | 500 |
| $Na_2S_2O_8$ (initiator) | 1 |
| Poly-N-vinylpyrrolidone (® K-30, BASF) | 10 |

The polymer was prepared by the gel polymerization method in water. The monomers were dissolved in water, the reaction mixture was rendered inert, and then, after initial heating to 65° C., the reaction was initiated by addition of sodium peroxodisulfate. The polymer gel was subsequently comminuted and the polymer was isolated by vacuum drying.

EXAMPLE 3

| Reactants | amount (g) |
|---|---|
| AMPS | 80 |
| ® Genapol-BE-020-methacrylate | 20 |
| Cyclohexane | 200 |
| Water | 300 |
| ® Span 80 | 1 |
| $Na_2S_2O_8$ (initiator) | 1 |
| Poly[N-vinylpyrrolidone-co-acrylic acid] (30/70) | 4 |

The polymer was prepared by the emulsion method in water. The monomers were emulsified in water/cyclohexane using ®Span 80, then the reaction mixture was rendered inert using $N_2$, and then, after initial heating to 80° C., the reaction was initiated by addition of sodium peroxodisulfate. The polymer emulsion was subsequently evaporated down (cyclohexane acting as azeotrope former for water) and the polymer was isolated.

EXAMPLE 4

| Reactants | amount (g) |
|---|---|
| $NH_3$-neutralized AMPS | 80 |
| MPEG-750 methacrylate | 15 |
| t-Butanol | 300 |
| TMPTA | 1.8 |
| AIBN (initiator) | 1 |
| Poly[N-vinylcaprolactone-co-acrylic acid] (10/90) | 10 |

The polymer was prepared by the precipitation method in tert-butanol. The monomers in t-butanol were introduced as an initial charge, the reaction mixture was rendered inert, and then, after initial heating to 60° C., the reaction was initiated by adding AIBN. The polymer was isolated by removing the solvent under suction and by subsequent vacuum drying.

The polymer showed a clear appearance with a viscosity of 65 000 mPas in 1% strength solution in distilled water. In comparison thereto, the unmodified gel of the same composition—only the polymeric additive is absent—exhibited a much more opalescent appearance and a viscosity of 50 000 mPas under identical measurement conditions.

EXAMPLE 5

| Reactants | amount (g) |
|---|---|
| Na-neutralized AMPS | 80 |
| MPEG-750 methacrylate | 15 |
| ® Genapol-O-150 methacrylate | 15 |
| Water | 300 |
| TMPTA | 1.8 |
| $H_2O_2$/iron (initiator) | 1 |
| Poly[N-vinylformamide] | 8 |

The polymer was prepared by the solution method in water. The monomers were dissolved in water, the reaction mixture was rendered inert, and then, after initial heating to 55° C., the reaction was initiated by means of an iron(II) sulfate/$H_2O_2$ redox couple. The polymer solution was subsequently evaporated down and the polymer was isolated by vacuum drying.

EXAMPLE 6

| Reactants | amount (g) |
|---|---|
| $NH_3$-neutralized AMPS | 80 |
| ® Genapol-LA-250 methacrylate | 15 |
| Monohydroxypolyacrylamide methacrylate (Mn = 1500) | 25 |
| t-Butanol | 500 |
| TMPTA | 1.8 |
| Dilauroyl peroxide | 2 |
| Poly[N-vinylcaprolactam] | 4 |

The polymer was prepared by the precipitation method in tert-butanol. The monomers in t-butanol were introduced as an initial charge, the reaction mixture was rendered inert, and then, after initial heating to 60° C., the reaction was initiated by addition of DLP. The polymer was isolated by removing the solvent under suction and by subsequent vacuum drying.

EXAMPLE 7

| Reactants | amount (g) |
|---|---|
| $NH_3$-neutralized AMPS | 30 |
| ® Genapol-LA-030 methacrylate | 70 |
| t-Butanol | 500 |
| Dilauroyl peroxide | 2 |
| Poly[N-vinylpyrrolidone] [® K15, BASF] | 12 |

The polymer was prepared by the solution method in tert-butanol. The monomers in t-butanol were introduced as an initial charge, the reaction mixture was rendered inert, and then, after initial heating to 70° C., the reaction was initiated by addition of DLP. The polymer was isolated by evaporating off the solvent and by subsequent vacuum drying.

EXAMPLE 8

| Reactant | amount (g) |
|---|---|
| NH₃-neutralized AMPS | 5 |
| Acrylamide | 10 |
| N-Vinylformamide | 10 |
| ® Genapol-LA-040 methacrylate | 75 |
| Isopropanol | 300 |
| Water | 200 |
| Dilauroyl peroxide | 2 |
| Poly[acrylic acid-co-N-vinylformamide] | 7 |

The polymer was prepared by the solution method in an isopropanol/water mixture. The monomers in isopropanol/water were introduced as an initial charge, the reaction mixture was rendered inert, and then, after initial heating to 55° C., the reaction was initiated by addition of potassium peroxodisulfate. The polymer was isolated by evaporating off the solvent mixture and by subsequent vacuum drying.

| Chemical identification of the products used | |
|---|---|
| TMPTA | trimethylolpropane triacrylate |
| AIBN | azoisobutyronitrile |
| DLP | dilauroyl peroxide |
| ® Genapol-T-250 methacrylate | methacrylic acid $C_{16}/C_{18}$ alcohol ethoxylate ester |
| ® Genapol-LA-070 methacrylate | methacrylic acid $C_{12}/C_{14}$ alcohol ethoxylate ester (7 EO) |
| NH₃-neutralized AMPS | 2-acrylamido-2-methyl-1-amido-opropanesulfonic acid - ammonium salt |
| ® Genapol-BE-020 methacrylate | methacrylic acid $C_{22}$ alcohol ethoxylate ester |
| ® Span 80 | sorbitan ester |
| MPEG-750 methacrylate | methacrylic acid methyl ethoxylate ester (750 g/mol) |
| ® Genapol-O-150 methacrylate | methacrylic acid oleyl ethoxylate ester |
| ® Genapol-LA-250 methacrylate | methacrylic acid $C_{12}/C_{14}$ alcohol ethoxylate ester (25 EO) |
| ® Genapol-LA-030 methacrylate | methacrylic acid $C_{12}/C_{14}$-alcohol ethoxylate ester (3 EO) |
| ® Genapol-LA-040 methacrylate | methacrylic acid $C_{12}/C_{14}$-alcohol ethoxylate ester (4 EO) |

The ® Genapol products are from Clariant GmbH.

What is claimed is:

1. A water-soluble or water-swellable grafted comb copolymer obtained by free-radical copolymerization of
   A) acryloyldimethyltaurine or acryloyldimethyltaurates or mixtures thereof,
   B) optionally, one or more other olefinicaily unsaturated, comonomer containing at least one oxygen, nitrogen, sulfur or phosphorus atom and possessing a molecular weight of less than 500 g/mol,
   C) one or more macromonomer of fomula (II)

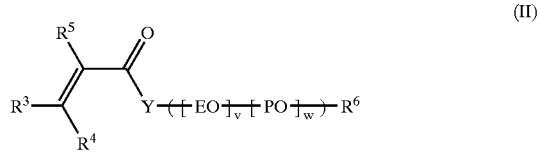

(II)

in which $R^3$, $R^4$, $R^5$, and $R^6$ independently of one another denote hydrogen, n-alliphatic, iso-alliphatic, cycloalliphatic, olefinic, arylalliphatic and/or aromatic radicals having a carbon number of from 1 to 30, Y is a bridging group, and v and w independently of one another are from 0 to 500, the sum of v and w being on average $\geq 1$;
   D) the copolymerization taking place in the presence of at least one polymeric additive having a number-average molecular weight of from 200 g/mol to $10^9$ g/mol to provide graft copolymerization.

2. The water-soluble or water-swellable grafted comb copolymer as claimed in claim 1, further comprising a compound of formula (I)

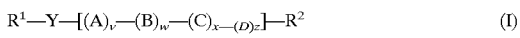

(I)

where R1 represents a polymerizable function from the group of the vinylically unsaturated compounds;
   Y is a bridging group,
   A, B, C, and D independently of one another are discrete chemical repeating units,
   v, w, x, and z independently of one another amount to from 0 to 500, the sum of v, w, x, and z being on average $\geq 1$; and
   $R^2$ is a linear or branched alliphatic, olefinic, cycloalliphatic, arylalliphatic or aromatic ($C^1$–$C^{50}$) hydrocarbon radical, OH, —$NH_2$ or —$N(CH_3)_2$ or is [—Y—$R^1$].

3. The water-soluble or water-swellable grafted comb copolymer of claim 1, further containing one or more comonomers B).

4. The water-soluble or water-swellable grafted comb copolymer as claimed in claim 1, wherein the comonomer B) is selected from the group consisting of unsaturated carboxylic acids, salts of unsaturated carboxylic acids, anhydrides of unsaturated carboxylic acids, esters of unsaturated carboxylic acids with alliphatic, olefinic, cycloalliphatic, arylalliphatic or aromatic alcohols having 1 to 22 carbon atoms, open-chain N-vinyl amides, cyclic N-vinyl amides having a ring size of from 3 to 9, amides of acrylic acid, amides of methacrylic acid, amides of substituted acrylic acids, amides of substituted methacrylic acids, 2-vinylpyridine, 4-vinylpyridine, vinyl acetate; styrene, acrylonitrile, vinyl chloride, vinylidene chloride, tetrafluoroethylene, vinylphosphonic acid or the esters or salts thereof, vinylsulfonic acid or the esters or salts thereof, allylphosphonic acid or the esters or salts thereof, methallylsulfonic acid or the esters or salts thereof, and mixtures thereof.

5. The water-soluble or water-swellable grafted comb copolymer of claim 1, wherein the polymeric additives D) is selected from the group consisting of polyalkylene glycol, alkylpolyglycol, and mixtures thereof or a homopolymer or copolymer of a compound selected from the group consisting of N-vinylformamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxymethyl methecrylate, diallyldimethylammonium chloride (DADMAC), [2-(methacryloyloxy)ethyl] trimethylammonium chloride (MAPTAC), and mixtures thereof.

6. The water-soluble or water-swellable grafted comb copolymer as claimed in claim 5, wherein the polymeric additive D) is selected from the group consisting of poly (N-vinylformamides), poly(N-vinylcaprolactams), copolymers of N-vinylpyrrolidone. N-vinylformamide, acrylic acid, and mixtures thereof.

7. The water-soluble or water-swellable grafted comb copolymer of claim 1, wherein said copolymer is crosslinked.

8. The water-soluble or water-swellable grafted comb copolymer of claim 1, wherein said copolymerization is prepared by precipitation polymerization in tert-butanol.

9. The water-soluble or water-swellable grafted comb copolymer of claim 2, wherein $R^1$ is a radical selected from the group consisting of vinyl, allyl, methallyl, methylvinyl, acryloyl, methacryloyl, crotonyl, seneclonyl, itaconyl, maleyl, fumaryl, styryl, and mixtures thereof.

10. The water-soluble or water-swellable grafted comb copolymer of claim 1, wherein the chemical bridge Y is selected from the group consisting of O—, —S—, —C(O)—, —O—CH$_2$—CH(O—)—CH$_2$OH, —O—CH$_2$—CH(OH)—CH$_2$O—, —O—SO$_2$O—, —O—SO$_2$—O—, —O—SO—O—, —PH—, —P(CH$_3$)—, —PO$_3$—, —NH—, —N(CH$_3$), and mixtures thereof.

11. The water-soluble or water-swellable grafted comb copolymer of claim 2, wherein the repeating units A, B, C, and D originate from the group consisting of acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethytacrylamide, diisopropylacrylamide, and mixtures thereof.

12. The water-soluble or water-swellable grafted comb copolymer of claim 2, wherein the repeating units A, B, C and D originate from ethylene oxide and/or propylene oxide.

13. The water-soluble or water-swellable grafted comb copolymer of claim 2, wherein v, w, x, and z independently of one another amount to from 1 to 30.

14. The water-soluble or water-swellable grafted comb copolymer of claim 1, wherein v and w independently of one another amount to from 1 to 30.

15. A water-soluble or water-swellable grafted comb copolymer obtained by free-radical copolymerization of acryloyldimethyltaurine and/or acryloyldimethyltaurate, with or in the presence of at least one component selected from the group consisting of:

a) one or more macromonomer of formula (II)

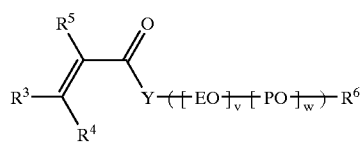

(II)

in which $R^3$, $R^4$, $R^5$, and $R^6$ independently of one another denote hydrogen, n-alliphatic, iso-alliphatic, cycloalliphatic, olefinic, arylalliphatic and/or aromatic radicals having a carbon number of from 1 to 30, Y is a bridging group, and v and w independently of one another are from 0 to 500, the sum of v and w being on average $\geq 1$, and b) at least one polymeric additive having a number-average molecular weight of from 200 g/mol to $10^9$ g/mol to provide graft copolymerization.

16. The water-soluble or water-swellable grafted comb copolymer of claim 15, further comprising one or more olefinically unsaturated, noncationic comonomer containing at least one oxygen, nitrogen, sulfur or phosphorus atom and having a molecular weight of less than 500 g/mol.

17. The water-soluble or water-swellable graft comb copolymer of claim 16, wherein the comonomer is crosslinking.

18. The water-soluble or water-swellable grafted comb copolymer of claim 16, wherein the macromonomer is crosslinking.

19. A water-soluble or water-swellable grafted comb copolymer obtained by free-radical copolymerization of A) acryloyldimethyltaurine or acryloyldimethyltaurates or mixtures thereof, B) optionally, one or more other olefinically unsaturated, comonomer containing at least one oxygen, nitrogen, sulfur or phosphorus atom and possessing a molecular weight of less than 500 g/mol, C) one or more macromonomer of formula (II)

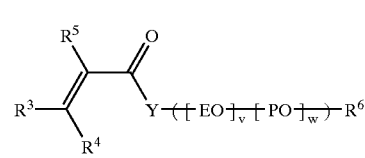

(II)

in which $R^3$ and $R^4$ are hydrogen or —CH$_3$, $R^5$ is hydrogen or —CH$_3$, and $R_6$ is an n-aliphatic, iso-alliphatic, cycloalliphatic, olefinic, arylalliphatic or aromatic hydrocarbon radical having a carbon number of from 1 to 30, Y is a bridging group, and v and w independently of one another are from 0 to 500, the sum of v and w being on average $\geq 1$;

D) the copolymerization taking place in the presence of at least one polymeric additive having a number-average molecular weight of from 200 g/mol to $10^9$ g/mol, said polymeric additive being a homopolymer or copolymer or a mixture of a homopolymer and a copolymer of one or more compounds selected from the group consisting of N-vinylformamide, N-vinylacetamide, N-vinylpyrrolidone, acryloyldimethyltaurine, N-vinylcaprolactam, N-vinylmethylacetamide, acrylamide, acrylic acid, methacrylic acid, N-vinylmorpholide, hydroxymethyl methacrylate, diallyldimethylammonium chloride (DADMAC), [2-(methacryloyloxy)ethyl]trimethylammonium chloride (MAPTAC), and mixtures thereof to provide graft copolymerization, and wherein the said acryloyldimethyltaurine or salt thereof has a degree of neutralization above 80 percent.

20. A water-soluble or water-swellable grafted comb copolymer obtained by free-radical copolymerization of A) acryloyldimethyltaurine or acryloyldimethyltaurates or mixtures thereof, B) optionally, one or more other olefinically unsaturated, comonomer containing at least one oxygen, nitrogen, sulfur or phosphorus atom and possessing a molecular weight of less than 500 g/mol, C) one or more macromonomer of formula (II)

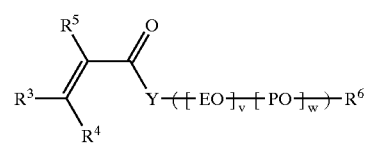

(II)

in which $R^3$ and $R^4$ are hydrogen or —CH$_3$, $R^5$ is hydrogen or —CH$_3$, and $R^6$ is an n-aliphatic, iso-aliphatic, cycloaliphatic, olefinic, arylaliphatic or aromatic hydrocarbon radical having a carbon number of from 1 to 30, Y is a bridging group, and v and w independently of one another are from 0 to 500, the sum of v and w being on average $\geq 1$;

E) the copolymerization taking place in the presence of at least one polymeric additive having a number-average molecular weight of from 200 g/mol to $10^9$ g/mol and mixtures thereof to provide graft copolymerization, and wherein the said acryloyldimethyltaurine or salt thereof has a degree of neutralization above 80 percent.

* * * * *